(12) United States Patent
Wang et al.

(10) Patent No.: US 6,596,543 B2
(45) Date of Patent: Jul. 22, 2003

(54) USE OF LIPOSOMES OF DEFINED COMPOSITION AND SIZE FOR THE PREPARATION OF PROTHROMBIN TIME REAGENTS

(75) Inventors: Jianfang Wang, Wilmington, DE (US); Kevin Bruce Johnson, Miami, FL (US); Liliana Maria Tejidor, Raleigh, NC (US); Hema Doobay, Raleigh, NC (US)

(73) Assignee: Dade Behring Inc., Deerfield, IL (US)

( * ) Notice: Subject to any disclaimer, the term of this patent is extended or adjusted under 35 U.S.C. 154(b) by 30 days.

(21) Appl. No.: 09/815,398

(22) Filed: Mar. 22, 2001

(65) Prior Publication Data

US 2002/0182225 A1 Dec. 5, 2002

(51) Int. Cl.$^7$ ................. G01N 33/86; A61K 9/127; A61K 9/64; A61K 35/14
(52) U.S. Cl. ................. 436/69; 424/1.21; 424/9.1; 424/9.321; 424/9.322; 424/450; 424/460; 530/381
(58) Field of Search ................. 436/69; 424/1.21, 424/9.1, 9.321, 9.322, 450, 460; 530/381

(56) References Cited

U.S. PATENT DOCUMENTS

| | | | |
|---|---|---|---|
| 3,179,567 A | 4/1965 | Owren ................. 435/13 |
| 4,873,089 A | 10/1989 | Scotto et al. ................. 424/450 |
| 5,023,087 A * | 6/1991 | Yau-Young ................. 424/450 |
| 5,314,695 A | 5/1994 | Brown ................. 424/450 |
| 5,599,909 A | 2/1997 | Fickenscher et al. ........ 530/402 |
| 5,625,036 A | 4/1997 | Hawkins et al. ............ 530/381 |
| 5,698,677 A | 12/1997 | Eibl et al. ................. 530/381 |
| 5,741,658 A | 4/1998 | Morrissey ................. 435/23 |
| 6,203,816 B1 * | 3/2001 | Brown ................. 424/450 |
| 6,248,353 B1 * | 6/2001 | Singh ................. 424/450 |

FOREIGN PATENT DOCUMENTS

| EP | 0 566 333 A1 | 10/1993 |
| WO | WO 93/07492 | 4/1993 |

OTHER PUBLICATIONS

Wang et al. Use of liposomes of defined composition and size for the preparation of prothrombin time reagents, Clinical Chemistry. Jun. 2000, vol. 46, No. 6, part 2, Suppl. p. A134, Abstract No. 516.*

Crowe, John H., Crowe Lois M., Biochimica et Biophysica Acta 939 (1988) 327–334 Factors affecting the stability of dry liposomes.

Morrissey, J.H.,Fakhrai,H., Edgington, T.S., Cell, vol. 50, 1987, 129–135 Molecular Cloning of the cDNA for Tissue Factor, the Cellular Receptor for the Initiation of the Coagulation Protease Cascade.

Litzinger, D.C., Buiting, A.M.J., van Rooijen, N., Huang, L., Biochimica et Biphysica Acta 1190 (1994) 99–107 Effect of liposome size on the circulation time and intraorgan distribution of amphipathic poly(ethylene glycol)–containing liposomes.

Spicer, E.K., Horton, R., Bloem, L., Bach, R., et al, Proc. Natl. Acad. Sci. USA vol 84, (1987) 5148–5152, Biochemistry Isolation of cDNA clones coding for human tissue factor: Primary structure of the protein and cDN.

Bader, R. Mannucci, P.M. M., Tripodi, A. Hirsh, J., et al, Thrombosis and Haemostasis, 1994, (3) 292–299 Multicentric Evaluation of a New PT Reagent Based on Recombinant Human Tissue Factor and Synthetic Phospholipids.

Rehemtulla, A., Pepe, M., Edgington, T.S., Thrombosis and Haemostasis, 1991, vol 65, 521–527 High Level Expression of Recombinant Human Tissue Factor in Chinese Hamster Ovary Cells as a Human Thromboplastin.

Lasic, D.D., Phys. to Applications, Elsevier Science B. V., the Netherlands, 1993, pp. 34, 275, and 556–558 Liposomes.

Hawkins, P. Tejidor, L.P.,Estevez, R., Johnson, K., et al, Thrombosis and Haemostasis, 1991, vol 65, 1215 Prothrombin time reagents prepared from recombiant human tissue factor produced in *E. coli*.

* cited by examiner

*Primary Examiner*—Christopher S. F. Low
*Assistant Examiner*—Holly Schnizer
(74) *Attorney, Agent, or Firm*—Cynthia G. Tymeson

(57) ABSTRACT

The present invention relates generally to the field of prothrombin time reagents for determining dysfunction in the coagulation system and more specifically to reagents made from native thromboplastin or purified or recombinant tissue factor and phospholipids from a natural or synthetic source. The present invention relates to methods to make a diagnostic reagent that includes a membrane-bound protein incorporated into a liposome and having additional empty liposomes (liposomes without membrane-bound protein incorporated therein) added to the solution.

9 Claims, No Drawings

USE OF LIPOSOMES OF DEFINED COMPOSITION AND SIZE FOR THE PREPARATION OF PROTHROMBIN TIME REAGENTS

FIELD OF THE INVENTION

The present invention relates generally to the field of prothrombin time reagents for determining dysfunction in the coagulation system and more specifically to reagents made from native thromboplastin or purified or recombinant tissue factor and phospholipids from a natural or synthetic source.

BACKGROUND OF THE INVENTION

Tissue factor is a membrane-associated glycoprotein which functions by forming a complex with blood coagulation factors VII and VIIa. The complexing of these factors greatly enhances the proteolytic activity of factors VII and VIIa. Functional activity of tissue factor has an absolute dependence on the presence of phospholipids. Bach, Ronald R. *Initiation of Coagulation by Tissue Factor*. CRC Critical Reviews in Biochemistry 1988:23(4): pp. 339–368. The factor VII/VIIa/tissue factor complex activates a series of specific enzymes that comprise the extrinsic and common pathways of the coagulation cascade ultimately leading to the formation of thrombin, fibrin, platelet activation and finally clot formation.

Diagnostic tests such as the prothrombin time (PT) test, utilize this series of enzymatic events in vitro under controlled conditions to diagnose dysfunction in the blood coagulation system of patients. In the PT test, the time it takes for clot formation to occur is the prothrombin time or PT value.

There are many commercially available PT reagents. They contain membrane-bound proteins, for example tissue factor, incorporated into liposomes. Some are crude tissue factor preparations (thromboplastins) extracted from rabbit brain, rabbit brain/lung mixtures, human placenta or ox brain. Others are based on purified or recombinant tissue factor (human, rabbit etc) combined with phospholipids. The protein/phospholipid mixture or crude thromboplastin extract is generally also combined with calcium ion and buffers. The final reagents may include stabilizers such as glycine, dextrans, detergents and the like and salts such as sodium chloride.

Methods for incorporating, i.e., reconstituting, proteins into liposomes are known in the art. See Rigaud, J-L., et al., "Liposomes as Tools for the Reconstitution of Biological Systems," p. 71–88, in Liposomes as Tools in Basic Research and Industry, ed. Philippot, J. R. and Schuber, F., CRC Press, Boca Raton, Fla. (1995). One method is disclosed in U.S. Ser. No. 09/459,137 filed Dec. 10, 1999, incorporated herein by reference in its entirety, which describes a method to incorporate membrane proteins into liposomes without the use of detergents. The method comprises providing the membrane protein in solution, then providing a solution of preformed liposomes; and incubating the mixture. Prior to the step of providing a solution of preformed liposomes, the liposomes are formed by combining a mixture of phospholipids with a solution of at least one type of unsaturated fatty acid. U.S. Ser. No. 09/459,137 discloses that it is preferred that the liposomes have a generally uniform size. In general, the smaller and larger liposomes, e.g., 50 nm and 400 nm, show a longer clotting time. In U.S. Ser. No. 09/459,137 it is disclosed that the liposomes may have a preferred size ranging from 75 to 150 nm, most preferably about 100 nm. U.S. Ser. No. 09/459,137 also discloses that addition of phospholipids and fatty acids into the tissue factor reagent modulates the clotting activity.

SUMMARY OF THE INVENTION

The present invention relates to methods to make a diagnostic reagent that includes a membrane-bound protein incorporated into a liposome and having additional empty liposomes (liposomes without membrane-bound protein incorporated therein) added to the solution.

DETAILED DESCRIPTION OF THE INVENTION

The present invention relates to methods of preparing diagnostic reagents that include liposomes as a constituent. The liposomes used in the present invention are selected and prepared to have a particular and/or known mean size. The present invention also includes diagnostic reagent compositions comprising liposomes selected as to have a particular mean size. The present method enables the preparation of such reagents, such as prothrombin time (PT) reagents and Activated partial thromboplastin times (APTT), having improved performance and improved manufacturability compared with currently available PT or APTT reagents. After a reagent is formulated and prepared it may lack certain characteristics such as the time it takes to clot certain types of samples (e.g. normal and abnormal samples or controls). In this method liposomes of a uniform size are added to current formulated reagents as an additional step in the manufacturing process after the membrane-bound protein has been incorporated into liposomes. If necessary, additional buffer and stabilizers may also be added after this step. The added liposomes are sometimes referred to herein as "empty liposomes" to distinguish them from liposomes that have the membrane-bound protein incorporated therein.

The liposomes used in the present invention may be synthetic or natural and include without limitation saturated or unsaturated mono or disubstituted fatty acids and combinations thereof. These phospholipids may include dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoeoylphosphatidylcholine, palmiticlinoeoylphosphatidylserine, palmiticlinoeoylphosphatidylethanolamine, palmiticlinoeoylphosphatidylglycerol, palmiticlinoleoylphosphatidic acid These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. Preferably, the mixture of phospholipids comprises dioleoylphosphatidylcholine (1,2 Dioleoyl-sn-glycero-3-phosphocholine) ("DOPC") and dioleoylphosphatidylserine ("DOPS") or 1-Palmitoyl-2-Oleoyl-sn-glucero-3-phosphoserine ("POPS") in a ratio of from about 5 to about 1. In preferred methods, the DOPC and DOPS or POPS are in a ratio of from about 7 to about 3. In preferred methods the phospholipids are synthetic. Synthetic phospholipids are readily available commercially from various sources, such as AVANTI Polar Lipids (Albaster, Ala.); Sigma Chemical Company (St. Louis, Mo.).

In one embodiment of the present invention, the mean sized liposomes are added to current PT or APTT reagent compositions to adjust the clotting activity and sensitivity during the manufacturing process. The final reagent is active as demonstrated by showing clotting activity which is comparable to that of optimized current reagents.

Naturally occurring phospholipids used to prepare liposomes for use in a PT reagent containing recombinant or native TF include natural phosphatidyl serine (PS) suitably in the range 2.5–50 mole % ("%"), generally in the range from about 25 to 35% of total phospholipid with the most common at about 30% and natural phosphatidyl choline (PC) suitably in the range from 20–95%, generally in the range from about 65 to 75% of total phospholipid with the most common at about 70%. The phosphatidylcholine used is neutral in charge, while the phosphatidylserine is negatively charged. In the preferred embodiment the lipid mixture has at least one component with a net negative charge. In other embodiments of this invention it is possible to use combinations of other lipids. A preferred source of the natural PS is from bovine brain and a preferred source of the natural PC is from egg yolk. Phosphatidyl glycerol (PG) and phosphatidyl ethanolamine (PE) can also be used in the liposome composition at percentages known in the art. For instance, it is disclosed in U.S. Pat. No. 5,314,695 that PG may be in the range from 0–40% and, if included, PE in the range from 2.5–50%. Collectively the phospholipids are designated herein as PL.

Synthetic phospholipids may also be used with the present invention and are preferred. These synthetic compounds may be varied and may have variations in their fatty acid side chains not found in naturally occurring phospholipids. The side chain variations that result in PT reagent improvement are listed above. Preferred compounds have unsaturated fatty acid side chains with C14, C16, C18 or C20 chains length in either or both the PS or PC. Preferred compositions include but are not limited to those that have dioleoyl (18:1)-PS; palmitoyl (16:0)-oleoyl (18:1)-PS, dimyristoyl (14:0)-PS, dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. PE and PG may also be included. The ratios of PS and PC and, if included, PE and/or PG, to total lipid are the same as those used with natural lipids.

Improved activity of the reagent is achieved by adding to current compositions, liposomes selected as to having a uniform size at particular concentrations. Thus, the liposome size and concentration are used to achieve and maintain optimal functional activity making the manufacturing process less susceptible to manufacturing error and/or waste. The size of the liposomes in the current compositions may vary from less than 50 to over 400 nm.

The liposomes used in the present invention may be prepared as follows:

PL solutions are commercially available stored in organic solvents such as chloroform. The correct amounts of each PL are combined. Prior to use, the organic solvents are removed by standard methods and anti-oxidants added. The PL mixture is resolubilized in a buffer such as Tris or HEPES/saline. Dried PL mixture with preferred PL composition can also be specifically made by AVANTI Polar Lipids (Albaster, Ala.). This dried PL mixture can be directly resolubilized in buffer prior to extrusion. Liposomes are then prepared by extrusion. The filter size and number of passes determine the mean size. See, for instance, Litzinger et al., *Effect of Liposome Size on the circulation time and intraorgan distribution of amphipathIC poly(ethylene glycol)—containing liposomes.* Biochimica et Biophysica Act 1190 (1994) 99–107. To obtain liposome of different sizes, aliquots of liposomes are taken at different passes during the extrusion process. Liposome size of each aliquot can be measured by using light scattering.

The differing sized liposome solutions are combined with either natural or recombinant tissue factor reagent or other membrane bound protein-based reagent, such as an APPT reagent. Generally in a certain range of the liposome mean size the smaller the liposome size, the less liposome is required to achieve the same test characteristics such as how the reagent measures frozen normal plasmas (FNP) and oral anticoagulant coumarin samples (CUM).

In preferred embodiments of the present invention, the membrane protein to be incorporated into the liposome is tissue factor. Preferably the tissue factor that is used in the present methods is a recombinant tissue factor as described by Hawkins, P. L., et al. (U.S. Pat. No. 5,625,136), incorporated herein in its entirety. As discussed above, the use of recombinant tissue factor, as opposed to crude tissue factor from natural sources such as rabbit brain, rabbit brain/lung mixtures, human placenta or ox brain, eliminates problems associated with these sources. The tissue factor was cloned in *E. coli* by procedures similar to that described by Fisher K. L., et al., Cloning and expression of human tissue factor cDNA. Thromb. Res. (1987) 48: 89–99 and Morrissey J. H., et al., Molecular cloning of the cDNA for tissue factor, the cellular receptor for the initiation of the coagulation protease cascade, Cell (1987) 50: 129–135.

The preferred embodiment of the present invention uses well-defined, purified proteins, e.g., rTF, prepared by standard techniques to provide a PT reagent in combination with liposomes of a uniform size. Full length as well as truncated recombinant molecules can be used and are prepared pursuant to methods known in the art, e.g., methods of Nemerson and Pabrosky (Spicer E. K., et al. Isolation of cDNA clones coding for human tissue factor: primary structure of the protein and cDNA, Proc. Natl. Acad. Sci. USA (1987) 84: 5148–52; Pabrosky, L., et al. Purification of recombinant human tissue factor. Biochemistry (1989) 28: 8072–77; Fisher K. L., et al. Cloning and expression of human tissue factor cDNA. Thromb. Research (1987) 48: 89–99.); The present invention also encompasses proteins, e.g., rTF, with additions, deletions and substitutions of amino acids that do not diminish the functional activity of the reagent. In a preferred embodiment, the preferred modification of rTF is truncated at or about amino acid residue 243. The preferred concentrations of rTF in the PT reagent are from about 20 to 400 ng/mL and most preferably about 100 to 350 ng/mL. PT reagents made from these raw materials are optically clear without the fine precipitates found in PT reagents based on crude extracts of natural source materials. Since the raw materials are highly purified, chemical analysis gives a meaningful measure of their expected performance. Chemical analysis, in combination with functional assays, provides lot-to-lot consistency, an important clinical consideration.

The PT reagents made from recombinant or natural purified tissue factor in combination with natural phospholipids and synthetic phospholipids of and without variation in side chains of uniform size offers an improvement in the quality and sensitivity of the PT reagent by allowing the use of less of the more costly membrane protein. Synthetic phospholipids give the advantage of a more reproducible final product and offer the improvement of better-controlled functional activity of the PT reagent when the side chains are varied.

The choice of buffers and stabilizers vary widely and can also assist in the stability of the PT reagent. The most preferred embodiments may include calcium ion in the concentration range form about 9 to 15 mM, NaCl in the concentration range from about 0 to 10% with the most preferred range from about 6 to 9%, dextran in the range of about 0 to 5%, a protein such as bovine gamma globulin or bovine serum albumin in the concentration range of about 0–5%; and an appropriate buffer. Buffers, such as N-2-Hydroxyethylpiperazine-N'-2-aminoethane sulfonic acid (HEPES), 3-[N-Bis{Hydroxymethyl}methylamino]-2-hydroxy-propane sulfonic acid (TAPSO), 3-(N-Morpholino) propane sulfonic acid (MOPS), N-Tris-(hydroxymethyl) methyl-2-aminoethanesulfonic acid (TES), 3-[N-bis (hydroxyethyl)-amino]2-hydroxypropane sulfonic acid (DIPSO), Piperazine-N,N'-bis(2-hydroxypropane-sulfonic acid) (POPSO), N-Hydroxyethylpiperazine-N'-2-hydroxypropane sulfonic (HEPPSO) and Tris-(hydroxymethyl)aminomethane (TRIS) are preferred in the PT reagent. The most preferred buffers are HEPES or TAPSO in the concentration range of about 20 to 80 mM.

In the preferred embodiment of this invention, the raw material recombinant human tissue factor is grown in vitro in E. coli, extracted with a detergent solution and then purified using affinity chromatography methods on immobilized monoclonal antibodies directed against human tissue factor. Bach, Ronald R., *Initiation of Coagulation by Tissue Factor*, CRC Critical Reviews in Biochemistry, 1988; 23 (4):pp. 339–368.

The PT reagent can be prepared by any of the techniques known in the art. After preparation and determination of the clotting time and sensitivity, liposomes of a uniform size are added to optimize the reagent's performance. Preferably, the liposomes added to the PT reagent have a size ranging from 75 to 150 nm, most preferably about 100–125.

The PT reagent prepared and optimized using the uniform liposome of the present invention can be used in any PT assay for laboratories, emergency room physician office labs and home use. The type of instruments on which these reagents can be used are exemplified by the 700, 800, 1000, 1400 and 1600 series of instruments from Medical Laboratory Automation (MLA), CA540, CA1000 and CA6000 series of instruments from Sysmex, BFA, BCT and BCS series of instruments from Dade Behring, MDA 40 instrument from Organon Technica, ACL100, ACL 1000 and ACL 3000 series of instruments from Instrumentation Laboratories, the BM/Stago STA Series, and Coagucheck from Boehringer Mannheim/Roche. This list of instruments is for information only and is not intended to be exclusive. All other instruments that utilize principles of operation similar to those described here can also be used for these reagents.

The PT reagents prepared using the present invention show normal clotting times when run on the CA-6000 instrument from Sysmex. For example, when used with normal frozen plasma and Coumadine plasma, the PT reagent made according to the methods of the present invention showed clotting times of 14 and 35 sec, respectively. By varying the liposome size and by varying the liposome concentration, the activity of the reagent can be varied. Thus, the reagent activity can be adjusted by adjusting liposome concentration with optimized liposome size.

The following examples are provided to illustrate the present invention and are not intended in any way to limit the scope of the invention.

I. General Procedure

A. Preparation of Tissue Factor:

Recombinant tissue factor (rTF) present in *E.coli* paste is purified by passage over an immunoaffinity column. The immunoaffinity column (1.6×30 cm), is prepared by covalent coupling of anti-rTF monoclonal antibody to activated Agarose, and is equilibrated with 20 mM Tris-150 mM NaCl-0.5% octylglucoside, pH 7.40. A 15 mL solution of the rTF (containing 0.66 mg/mL protein in the column equilibration buffer), after initial purification over Q-Sepharose, is loaded on the affinity column. The protein which is adsorbed on the column is eluted first with 0.1 M acetic acid-150 mM NaCl-0.1% octylglucoside, pH 4.0 and then successively with 0.1 M acetic acid-150 mM NaCl, pH 3.0 buffer containing 0.1 and 2% octylglucoside. Protein fractions that elute in the pH 3.0 buffer are adjusted to pH 7.30 by addition of 0.5 M Tris. These fractions contained 2.3 and 5.9 mg protein, respectively. Both of these protein-containing fractions contain identical proteins, as tested on an SDS-PAGE gel. These fractions are pooled together and mixed with solid octylglucoside to achieve 2% final concentration of the detergent. The eluted protein solution containing the apoprotein rTF is a single species as tested by SDS-PAGE. Protein concentration is determined by using an extinction coefficient of 1.6 mg mL$^{-1}$ cm$^{-1}$.

Clear protein solution (0.2 mL) in buffer containing 2% octylglucoside, is precipitated with 1.0 mL of cold acetone and the precipitate is suspended in 0.4 mL of trifluoroethanol and diluted with 0.4 mL of 40 mM Hepes-160 mM NaCl, pH 7.40. Clear solutions are obtained when detergent-solubilized solution of the protein is diafiltered in an Amicon ultrafiltration system (YM-10) using 50 mM Hepes-0.5 M NaCl, pH 7.40, 50 mM Hepes, pH 7.40 containing 20% DMSO, 40% DMSO or 60% alcohol.

B. Preparation of Liposomes for Tissue Factor

A chloroform solution of dioleoylphosphatidylcholine (DOPC; 66 mg; 2.64 mL of 25 mg/mL) and dioleoylphosphatidylserine (DOPS; 28.8 mg; 2.88 mL of 10 mg/mL) is evaporated under a stream of nitrogen. The dry film of the phospholipids is dissolved in 2 mL hexane and organic solvent was removed again under a stream of nitrogen. The dried film of the phospholipids is suspended in 3.16 mL of 40 mM HEPES-160 mM NaCl and detergents, pH 7.40. The phospholipid suspension is sonicated for one minute in a cup horn followed by extrusion using several passes through a 100 nm membrane (Avestin Inc., Ottawa, Canada ) and only a uniform pass is utilized for each reagent that is prepared. Alternatively, dried lipids can be purchased commercially from such sources as Aventi. This dried lipids mixture can be directly resolubilized into buffer prior to relipidation or liposome preparation.

C. Reconstitution:

A solution (20–100 μL) of the apoprotein rTF is incubated with 500 μL of each of the phospholipid suspensions for one hour at 37° C. or overnight at 4° C. For testing on the CA-6000, the protein-phospholipid mixture is diluted in a buffer containing 40 mM Hepes-160 mM NaCl-0.2% BSA-0.2% dextran-4.5% glycine-11 mM CaCl$_2$, pH 7.40. Alternatively, rTF is combined with liposomes and diafiltrated using an Amicon diafiltration system as described in U.S. Pat. No. 5,625,136.

D. Preparation of Liposomes for use in Adjusting PT Reactants

Synthetic phospholipids were purchased from Avanit Polar Lipids (Albaster, Ala.). Stock phospholipids, 30%POPS/70%DOPC, were dissolved in buffer to a concentration of 30 mg/mL or 15 mg/mL. Liposomes were prepared by extrusion using LiposoFast system Avestin, Ottawa, Canada) or EmulsiFlex-C5 (Avestin, Ottawa, Canada) through either a 100 nm or 200 nm membrane filter. Liposome size was measured by light scattering on an N4 Plus particle size analyzer (Coulter). Liposome concentration was examined by phosphate assay.

I. Effect of Liposome Concentration on Clotting Times and Sensitivity of a PT Reagent To a standard PT reagent were added increasing amounts of liposomes. Then 100 uL of each composition was added to 50 uL of a normal plasma sample. The clotting times were measured on a CA 6000 automatic coagulation timer (Sysmex) at 37 C. The results are shown below in Table 1.

TABLE 1

Phospholipid concentration determines the PT and the sensitivity of a PT Reagent.

| Liposome Concentration (ug/mL) | FNP PT (sec) | CUM PT (sec) | Ratio CUM/FNP (sensitivity) |
|---|---|---|---|
| 0 | 10.3 | 19.9 | 1.93 |
| 50 | 10.7 | 23.0 | 2.15 |
| 100 | 11.3 | 25.1 | 2.22 |
| 150 | 11.8 | 27.9 | 2.36 |
| 200 | 12.4 | 30.3 | 2.44 |
| 250 | 13.0 | 32.6 | 2.51 |
| 300 | 13.6 | 34.8 | 2.56 |
| 350 | 14.2 | 37.9 | 2.67 |
| 400 | 14.8 | 39.7 | 2.68 |
| 450 | 15.2 | 42.6 | 2.80 |
| 500 | 16.0 | 44.6 | 2.79 |
| 550 | 16.4 | 46.6 | 2.84 |
| 600 | 17.0 | 48.6 | 2.86 |
| 700 | 17.6 | 51.4 | 2.92 |

II. Liposome Size vs. Concentration-100 nm vs. 200 nm Liposome Size

Liposomes containing 30 mg/ml of a 30% 1-Palmitoyl-2-Oleoyl-sn-glycero-3-phosphoserine/70% 1,2-Dioleoyl-sn-glycero-3phosphocholine (POPS/DOPC) mixture are extruded using LiposoFast system (Avestin, Ottawa, Canada) through either a 100 or 200 nm membrane filter respectively (Poretics, Livermore, Calif.). Liposome size is measured by light scattering technique on an N4 Plus particle size analyzer (Beckman-Coulter). The effect on the clotting activity of a PT reagent, to which the liposome preparations are added, is monitored by measuring FNP and CUM clotting times. The results show that liposomes with a mean size of about 125 nm requires only a concentration of 350 ug/ml of liposome to achieve the effect of liposomes with a mean size of about 200 nm using a concentration of 450 ug/ml of liposome. Representative results are shown in Table 2.

TABLE 2

Effect of size of liposomes and concentration on the clotting time

| Concentration of Liposome (ug/ml) | Size of preformed liposomes (Mean) | FNP (seconds) | CUM (seconds) |
|---|---|---|---|
| 350 | 125 nm | 14.0 | 35.8 |
| 350 | 203 nm | 13.2 | 32.8 |
| 400 | 125 nm | 14.2 | 36.9 |
| 400 | 203 nm | 13.4 | 34.3 |
| 450 | 125 nm | 14.5 | 38.5 |
| 450 | 203 nm | 13.9 | 35.8 |

Thus, the degree to which the sensitivity of a PT reagent is affected by the addition of liposome is dependent on the mean liposome size. The amount of liposomes required to achieve equivalent effects on the PT reagent also depends on the mean liposome size.

III. Liposome Size

Liposomes containing 30 mg/ml of a 30% 1-Palmitoyl-2-Oleoyl-sn-glycero-3-phosphoserine/70% 1,2-Dioleoyl-sn-glycero-3phosphocholine (POPS/DOPC) mixture are extruded using EmulsiFlex-C5 system (Avestin, Ottawa, Canada) through either a 100 filter (Poretics, Livermore, Calif. About 20 passes are done. Aliquots of liposomes with different mean size are taken at different passes during the extrusion process. The liposome size and clotting activities are then measured. Table 3 shows the differences in mean size liposomes. It can be seen that a preparation of 350 ug/mL liposomes of about 100–125 nm mean size prolonged normal clotting times to the same extent as a preparation of liposomes of 203 at 450 ug/mL (Compare, Table 2).

TABLE 3

LIPOSOME SIZE AT 350 UG/ML LIPOSOMES

| Lipsome Size | FNP | CUM |
|---|---|---|
| 102 NM | 14.0 | 34.6 |
| 103 nm | 14.0 | 34.5 |
| 116 nm | 13.7 | 34.2 |
| 121 nm | 13.6 | 34.0 |

IV. Effect of Changing Liposome Size in Prepared Reagent

Liposomes are prepared as described above using for the extrusion an EmulsiFlex-C5 with 21 passes through a 100 nm membrane filter. Aliquots are frozen at −70C. for stability testing. Freshly made liposomes having a mean size of about 106 nm and a prothrombin time with FNP of 14.5 seconds. Liposomes that are subjected to a single freeze/thaw cycle display an increase in mean size, the degree of which varied with thawing conditions. As liposome size increases (here due to freeze/thaw) the CUM decreases. While a constant liposome does not mean no change in liposome activity (as seen through FNP and CUM data), a change in liposome size results in a change in liposome activity (as seen through FNP and CUM data).

TABLE 4

LIPOSOME SIZE-FREEZE/THAW

| Preparation- 30 mg/mL PS/PC | Liposome Mean Size | FNP | CUM |
|---|---|---|---|
| FRESH | 106 nm | 14.5 | 36.3 |
| 3 days at −70 C. thaw at 37 C. | 126 nm | 13.6 | 34.3 |
| 3 days at −70 C. thaw at 2–8 C. | 159 nm | 13.3 | 33.6 |
| 3 days at −70 C. thaw at RT | 204 nm | 13.2 | 34.3 |

All references cited herein are incorporated in their entirety.

The invention has been described in detail with particular references to the preferred embodiments thereof. However, it will be appreciated that modifications and improvements within the spirit and scope of this invention may be made by those skilled in the art upon considering the present disclosure.

We claim:

1. A method of making a diagnostic reagent for measuring clotting times, the method comprising:

a) providing a solution of empty liposomes having a uniform size; and b) combining the liposomes with a solution comprising a membrane-bound protein incorporated into liposomes.

2. The method according to claim 1, wherein the mean empty liposome size is between about 100 to 150 nanometers.

3. The method according to claim 1, wherein the membrane-bound protein comprises purified or recombinant tissue factor.

4. The method according to claim 3, wherein the tissue factor is recombinant tissue factor.

5. The method according to claim 1, wherein the empty liposomes comprise a mixture of phospholipids comprises dioleoylphosphatidylcholine [DOPC] and dioleoylphosphatidylserine [DOPS) or 1-Palmitoyl-2-Oleoyl-sn-glycero-3-phosphoserine [POPS).

6. The method according to claim 5, wherein the PC and PS phospholipids are in a ratio of from about 4 to about 1.

7. The method according to claim 6, wherein the PC and PS phospholipids are in a ratio of from about 7 to about 3.

8. The method according to claim 1, wherein the empty liposomes are prepared from synthetic phospholipids.

9. The method according to claim 1, wherein the amount of empty liposomes combined with the solution comprising a membrane-bound protein incorporated into liposomes is sufficient to adjust the clotting time of the solution comprising a membrane-bound protein incorporated into liposomes.

* * * * *